US012594080B2

(12) United States Patent
Tang

(10) Patent No.: US 12,594,080 B2
(45) Date of Patent: Apr. 7, 2026

(54) MEDICAL DEVICE FOR CAUSING HEMOSTASIS OF BLOOD VESSEL

(71) Applicant: MICRO-TECH (NANJING) CO., LTD., Nanjing (CN)

(72) Inventor: Zhi Tang, Nanjing (CN)

(73) Assignee: MICRO-TECH (NANJING) CO., LTD., Nanjing (CN)

( * ) Notice: Subject to any disclaimer, the term of this patent is extended or adjusted under 35 U.S.C. 154(b) by 44 days.

(21) Appl. No.: 18/714,380

(22) PCT Filed: Feb. 25, 2022

(86) PCT No.: PCT/CN2022/078089
§ 371 (c)(1),
(2) Date: May 29, 2024

(87) PCT Pub. No.: WO2023/159520
PCT Pub. Date: Aug. 31, 2023

(65) Prior Publication Data
US 2025/0025182 A1     Jan. 23, 2025

(51) Int. Cl.
*A61B 17/122* (2006.01)
*A61B 17/128* (2006.01)

(52) U.S. Cl.
CPC ........ *A61B 17/122* (2013.01); *A61B 17/1285* (2013.01)

(58) Field of Classification Search
CPC .............. A61B 17/122; A61B 17/1285; A61B 2017/00477
See application file for complete search history.

(56) References Cited

U.S. PATENT DOCUMENTS

| | | | | |
|---|---|---|---|---|
| 2010/0152753 A1* | 6/2010 | Menn | ................... | A61B 17/083 |
| | | | | 606/158 |
| 2022/0160366 A1* | 5/2022 | Kuhn | ................... | A61B 17/122 |
| 2022/0167990 A1* | 6/2022 | Kuhn | ................... | A61B 17/122 |

FOREIGN PATENT DOCUMENTS

| | | |
|---|---|---|
| CN | 109805977 A | 5/2019 |
| CN | 110191684 A | 8/2019 |
| CN | 110638489 A | 1/2020 |
| CN | 216876472 U | 7/2022 |
| CN | 216876473 U | 7/2022 |
| CN | 217793203 U | 11/2022 |
| EP | 1328199 B1 | 6/2018 |
| WO | WO2020211725 A1 | 10/2020 |
| WO | WO2021004107 A1 | 1/2021 |
| WO | WO2021021397 A1 | 2/2021 |
| WO | WO2021087461 A2 | 5/2021 |

* cited by examiner

*Primary Examiner* — Brooke Labranche
(74) *Attorney, Agent, or Firm* — Mandar A. Joshi; Bret E. Field; Bozicevic, Field & Francis LLP

(57)     ABSTRACT

A medical device for causing the hemostasis of a blood vessel for use through an endoscope comprises: a handle; a sheath device, which is attached to the handle; a clamp device including a clamp housing provided on the distal end of the sheath device and at least two, in particular exactly two clamp arms; a control wire extending through the sheath device and reversibly movable in the distal and proximal direction; an actuator coupled to the proximal end of the control wire and actuable to reversibly move the control wire in the distal and proximal direction; wherein the clamp arms are each coupled to the distal end of the control wire.

12 Claims, 32 Drawing Sheets

MEDICAL DEVICE FOR CAUSING HEMOSTASIS OF BLOOD VESSEL

This application is the national phase of International Application No. PCT/CN2022/078089, titled "MEDICAL DEVICE FOR CAUSING HEMOSTASIS OF BLOOD VESSEL", filed on Feb. 25, 2022, the entire disclosure of which is incorporated herein by reference.

TECHNICAL FIELD

The present disclosure relates to a medical device for causing the hemostasis of a blood vessel for use through an endoscope.

BACKGROUND

Medical devices of this kind are known for example from EP 1328199 B1 and in particular used to treat gastrointestinal bleedings. Specifically, such devices are used to set clamps or clips to pinch a bleeding vessel applying sufficient constrictive force to the blood vessel so as to limit or interrupt blood flow there through.

The medical device known from EP 1328199 B1 comprises a handle and a sheath, which is attached to the handle. A control wire extends through the sheath and can be actuated by an actuator, which is coupled to the proximal end of the control wire to reversibly move the control wire in the distal and proximal directions. The medical device further includes a clamp device including a sleeve provided on the distal end of the sheath and a clip with two clamp arms is coupled to the distal end of the control wire by means of a J-hook. The clamp arms cooperate with the sleeve in such a way, that the clamp arms engage the front edge of the sleeve to be elastically deformed inwardly, thus being closed, when the control wire is pulled in the proximal direction, whereas the clamp arms are distally pushed out of the sleeve and automatically reopen due to their elastic restoring force, when the control wire is pushed in the distal direction. Since the clamp device can be repeatedly opened and closed, setting of the clamp device is possible in an easy way.

Once the clamp device is set at the correct position, the clamp arms must be locked in their closed state. For this purpose, openings are provided at the clamp arms, into which corresponding protrusions formed in the inner surface of the sleeve can engage. In order to lock the clamp arms in their closed state, the control wire is pulled in the proximal direction so far, that the protrusions come into engagement with the openings formed in the clamp arms.

Furthermore, the clamp device with the clamp arms and the sleeve can be disconnected from the rest of the medical device. In order to do so, the control wire is further pulled back, when the clamp device is completely closed, so that the J-hooks brake and thus the connection between the clamp arms and the control wire is interrupted. Moreover, by further pulling back the control wire, a retainer, which connects the control wire with the sleeve, is actuated in order to disconnect the retainer and thus the control wire from the sleeve.

SUMMARY

In view of this prior art it is the object of the present disclosure to provide a medical device of the above-mentioned kind that it is easy to operate as well as easy to manufacture and assemble and that works in a reliable manner.

This object is solved by a medical device that the clamp housing is directly and releasably connected to the connect tube in such a way that the clamp housing can be rotated relative to the connect tube about the longitudinal axis.

A medical device for causing the hemostasis of blood vessel comprises:

a handle;

a sheath device, which is attached to the handle;

a clamp device including a clamp housing provided on the distal end of the sheath device and at least two, in particular exactly two clamp arms;

a control wire extending through the sheath device and reversibly moveable in the distal and proximal direction;

an actuator coupled to the proximal end of the control wire and actuable to reversibly move the control wire in the distal and proximal direction;

where the clamp arms are each coupled to the distal end of the control wire and wherein the clamp device is actuable to open and close the clamp arms by a movement of the control wire such that a movement of the control wire in a proximal direction is translated into a closing movement of the clamp arms and a movement of the control wire in the distal direction is translated into an opening movement of the clamp arms;

where the sheath device comprises a sheath, preferably an extendable coiled sheath, and a connect tube, which defines a longitudinal axis and is fixedly connected to the distal end of the sheath;

where the clamp housing is directly and releasably connected to the connect tube in such a way that the clamp housing can be rotated relative to the connect tube about the longitudinal axis.

The present disclosure is based on the consideration to provide the possibility to rotate the clamp device relative to the sheath about the longitudinal axis in order to improve the flexibility regarding the position in which the clamp arms can grasp tissue inside the human body. Accordingly, setting the clamp device inside the human body can be adapted to the orientation of the blood vessel that should be pinched. A direct rotatable connection between the clamp housing and the connect tube leads to a compact design and a short structural length of the distal end of the medical device, as no intermediate element between the clamp housing and the connect tube, which is fixedly connected to the sheath, is necessary.

Accordingly, it is provided that the clamp housing can be rotated relative to the tube formed at the distal end of the sheath device, which connect tube is fixed in a torque-proof connection to the distal end of the sheath. On the other hand, the clamp arms can be connected to the clamp housing in a rotationally fixed manner with regard to the longitudinal axis. Furthermore, the clamp housing can be connected to the control wire equally in a torque-proof manner, so that a rotation of the control wire relative to the sheath device leads to a rotation of the clamp arms about the longitudinal axis, wherein the clamp housing is rotated relative to the connect tube of the sheath device. Accordingly, the actuator and the handle are preferably designed in such a way that the control wire can be rotated relative to the sheath device about its longitudinal axis.

According to a preferred embodiment of the present disclosure, the clamp housing and the connect tube are connected to each other by a push-in connection thus forming an overlapping section of the connect tube and the clamp housing, wherein the clamp housing as an inner element is pushed into the connect tube as an outer element or the connect tube as an inner element is pushed into the clamp housing as an outer element, and at least two through-apertures are formed in the overlapping section of the inner element located with an angular offset in the circumferential direction, wherein a ring groove facing inwardly is formed in the overlapping section of the outer element, and at least one connecting element is provided which engages through at least one through-apertures of the inner element into the ring groove of the outer element in order to connect the clamp housing to the sheath device such that the clamp housing can be rotated relative to the connect tube of the sheath device.

Accordingly, one of the two elements, namely the clamp housing or the connect tube, forming an outer or female element comprises a ring groove facing inwardly and the other element, forming an inner or male element, comprises through-apertures in the same axial region like the ring groove. By means of a connecting element engaging through the through-aperture into the ring groove, a rotatable connection between the two elements can be achieved, as the connecting element is fixed in the circumferential direction at the inner element by engaging into the through-aperture, but can rotate freely with respect to the outer element due to the engagement into a ring groove. Such a connection is space-saving and allows a compact design of the distal end section of the medical device.

The inner element and the outer element are preferably designed such that a clearance fit is realized between the two elements. Consequently, the push-in connection can be released easily and a rotation of the inner element relative to the outer element is possible without applying a significant force or momentum.

A release arrangement cooperating with each connecting element may be provided and can be actuated by moving the control wire into the proximal direction, when the clamp arms have been closed and, in particular, the control wire has been uncoupled from the clamp device in order to bring the connecting element(s) out of engagement from the ring groove of the outer element, thus releasing the clamp housing from the sheath device. This design is based on the consideration that, after the clamp has been set inside the human body, the clamp housing must be separated from the sheath device in order to retract the sheath device and the control wire arranged therein through the working channel of an endoscope out the human body, whereby the clamp device should remain inside the human body.

In concrete terms, the medical device may comprise exactly one connecting element, which has at least two, in particular exactly two connecting arms located with a regular angular offset in the circumferential direction, each of the connecting arms engaging through one corresponding through-aperture formed in the inner element into the ring groove formed in the outer element. Preferably, the connecting arms of the connecting element are formed such that they engage with clearance in the longitudinal direction and in the radial direction into the ring groove formed in the outer element. In this way, an easy rotation of the outer element relative to the inner element is possible without significant momentums or forces being necessary, wherein the clamp housing is releasably held at the connect tube.

The connecting element may be formed as a disc having a central opening and at least two, in particular exactly two connecting arms protruding radially outwardly. Accordingly, the connecting element may be provided as a disc having a central opening and two radially protruding connecting arms, that engage a trough corresponding through-apertures formed in the inner element and into the ring groove formed in the outer element, wherein the entire connecting element is formed as a planar disc.

Alternatively, the connecting element may comprise a proximal main section in the form of a disc having a central opening and at least two, in particular exactly two connecting arms extending distally therefrom, wherein engagement portions are formed at the distal ends of the connecting arms end extend radially outwardly through the through-apertures of the inner element into the ring groove formed in the outer element. In other words, the connecting element has a certain extension in the longitudinal directing and comprises a main section with a central opening, through which the control wire can pass, and connecting arms extending distally from this main section. At the distal ends of the connecting arms, engagement portions extend radially outwardly, thus projecting into the through-apertures and the ring groove. By means of such an offset in the longitudinal direction between the main section and the engagement portions, the connecting element is very elastic and can be brought out of engagement from the ring groove of the outer element by a small axial force applied on the main section into the proximal direction.

Additionally, the connecting element of this type can comprise two or more guiding arms extending distally from the main section. The guiding arms preferably are arranged between the connecting arms in the circumferential direction in order to guide the connecting element inside the sheath device.

The release arrangement may further comprise an intermediate tube enclosing the control wire and arranged between the connecting element and a coupling head formed at the distal end of the control wire so that the intermediate tube pushes the connecting element in the proximal direction when the control wire is moved in the proximal direction and the clamp arms have been closed in order to bring the connecting element out of engagement from the ring groove formed in the outer element, thus releasing the clamp housing from the connect tube. In other words, an intermediate tube may be provided between the distal end of the control wire, for example a coupling head formed at the distal end of the control wire. When the control wire is pulled in proximal direction and the clamp arms have been closed, the intermediate tube is sandwiched between the distal end of the control wire and the connecting element. Accordingly, a further movement of the control wire in the proximal direction pushes the connecting element proximally, thus deforming the connecting element such that the connecting arms come out of engagement from the ring groove. In particular, the distal ends of the connecting arms may be straightened so that the engagement portions face distally, when the clamp housing has been released from the sheath device.

Alternatively, at least two, in particular exactly two connecting elements may be provided in the form of resilient, elastically deformable connecting arms, wherein the distal ends of the connecting element are fixedly attached to the clamp housing and the free proximal ends of the connecting elements form engagement portions, each of which engages through a corresponding through-aperture formed in the inner element and into the ring groove formed in the outer element. Contrary to the previously discussed embodiments, the connecting elements are fixedly connected to the clamp housing. One connecting element is assigned to each through-aperture formed in the inner element.

The release arrangement may comprise a protrusion, that is arranged between and cooperates with the connecting elements in such a way that the protrusion presses against the connecting elements elastically deforming them outwardly, so that the engagement portions of the connecting elements are urged outwardly into engagement with a corresponding through-aperture and the ring groove, in order to connect the clamp housing to the sheath device, wherein the protrusion is coupled with and in particular fixedly provided on the control wire in such a way that, if after closing the clamp arms of the control wire is moved further in the proximal direction, the protrusion is moved together with the control wire out of engagement from the connecting elements with the result, that the latter are deformed inwardly by their elastic restoring force and the engagement portions of the connecting elements come out of engagement of the corresponding ring groove of the outer element to release the clamp housing from the sheath device. In other words, it may be provided that the connecting elements are biased towards an inner position, in which they are out of engagement from the corresponding ring groove of the outer element. By means of a protrusion formed at the distal end of the control wire, in particular formed by a coupling head formed at the distal end of the control wire, the connecting elements are urged into an outer position, in which the engagement portions engage into the ring groove formed in the outer element, thus holding the clamp housing at the distal end of the sheath device. When the control wire is pulled in the proximal direction so far that the protrusion comes out of engagement from the connecting elements, they deform automatically inwardly due to their elastic restoring force, so that the engagement portions move inwardly, thus coming out of engagement of the corresponding ring groove. In this way, the clamp housing can be released from the sheath device in a very reliable manner.

The distal ends of the connecting elements may be directed radially outwardly and may extend into corresponding holding apertures provided in the clamp housing. Preferably, the distal ends of the connecting element are fixed therein by welding, in particular by spot welding. The connecting elements may have a straight section following the distal end of the connecting elements, which is slanted inwardly with regard to the longitudinal axis of the clamp housing, wherein the slanting angle is preferably at about 5°. An inwardly bulged section may be provided at the proximal end of the connecting elements.

The connect tube and the sheath may we welded or brazed or pressed together.

According to a further elaboration of the present disclosure, the clamp arms may be coupled to the distal end of the control wire via a pivot pin extending through corresponding through-holes provided in the proximal end section of the clamp arms and being held at the distal end of the control wire.

The pivot pin may protrude laterally on both sides from the clamp arms and the distal end of the control wire and may be guided in the clamp housing such that the pivot pin cannot be rotated about the longitudinal axis of the clamp housing. In concrete terms, the clamp housing, which preferably defines an interior space, may have on its inner surface two sliding grooves extending in the longitudinal direction and arranged opposite each other in such a way that the end sections of the pivot pin engage into the sliding grooves. In this way, it is ensured, that the pivot pin cannot rotate about the longitudinal direction of the clamp housing relative to the clamp housing. In other words, a torque-proof direction between the pivot pin and the clamp housing with respect to the longitudinal direction is realized. The sliding grooves may have a rectangular cross-section.

Preferably, the clamp housing comprises two bearing arms extending in the distal direction from a clamp base in particular in the form of a sleeve, wherein, in particular, a guide pin is held between the two bearing arms. Accordingly, each clamp arm can be provided with a guide groove and the guide grooves of the clamp arms partially overlap each other, and the guide pin, which is attached to the clamp housing, can extend through the guide grooves in the overlapping parts thereof, so that by the engagement of the guide pin and the guide grooves, a movement of the control wire in the proximal direction is translated into a closing movement of the clamp arms and a movement of the control wire in the distal direction is translated into an opening movement of the clamp arms around the pivot axis.

The medical device may further be designed such that the control wire includes a coupling head at its distal end, wherein the coupling head comprises at least one pair of holding arms, which are moveable between a fixing position in which the holding arm encompass the pivot pin, thus holding the pivot pin in particular in a form-fit manner, and a disengaging position, in which the holding arms are spread apart from each other, thus releasing the pivot pin. The coupling head, in particular the holding arms of the coupling head may be received by a retaining groove formed in the clamp housing. Accordingly, the holding arms abut against the sidewalls of the retaining groove. In this way, a rotationally fixed connection between the control wire and the clamp housing is achieved via the coupling head, the pivot pin, which preferably engages into sliding grooves formed in the clamp housing, and the holding arms, being received in retaining grooves. Accordingly, a rotation of the control wire relative to the sheath device caused by the actuator leads to a rotation of the clamp housing and, consequently, of the clamp arms about the longitudinal axis of the connect tube relative thereto.

BRIEF DESCRIPTION OF DRAWINGS

Embodiments of the present disclosure will in the following be described making reference to the attached drawing. In this drawing shows.

7

Figure 1:
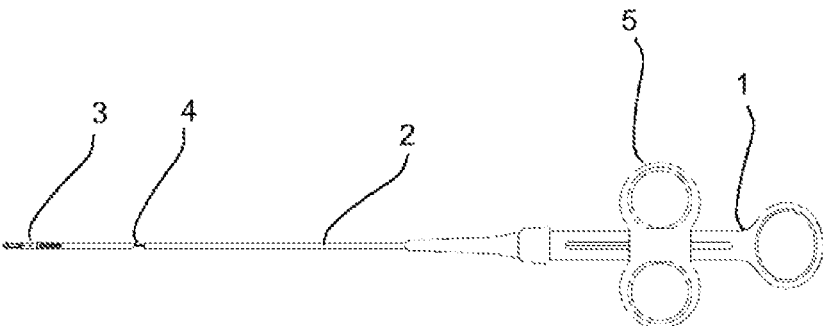
FIG. 1 a front view of a medical device according to a first embodiment of the present disclosure.
Figure 2:
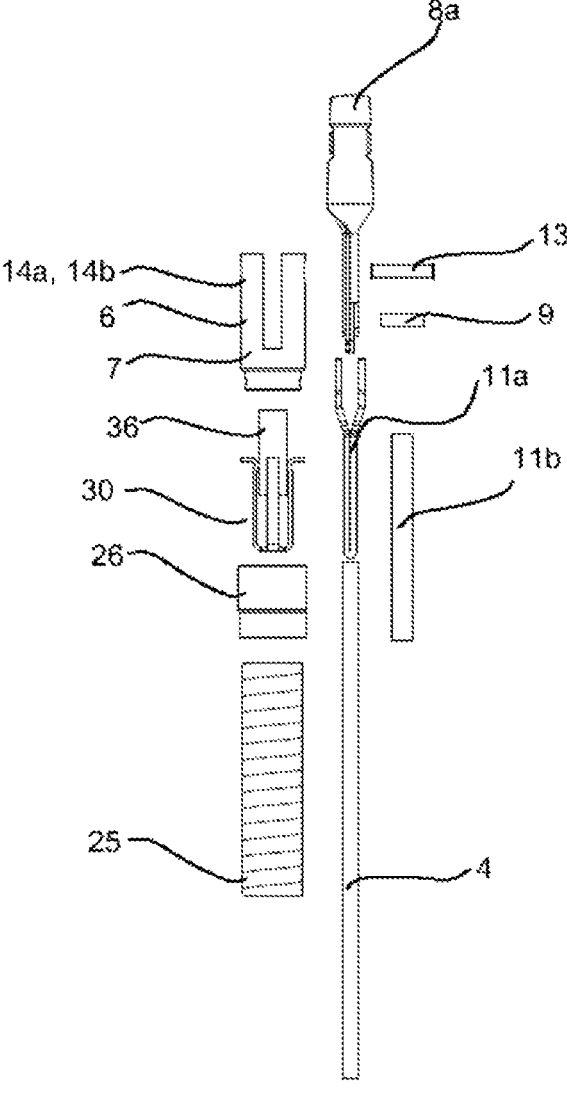
FIG. 2 an exploded view of the distal end of the medical device of FIG. 1.
Figure 3:
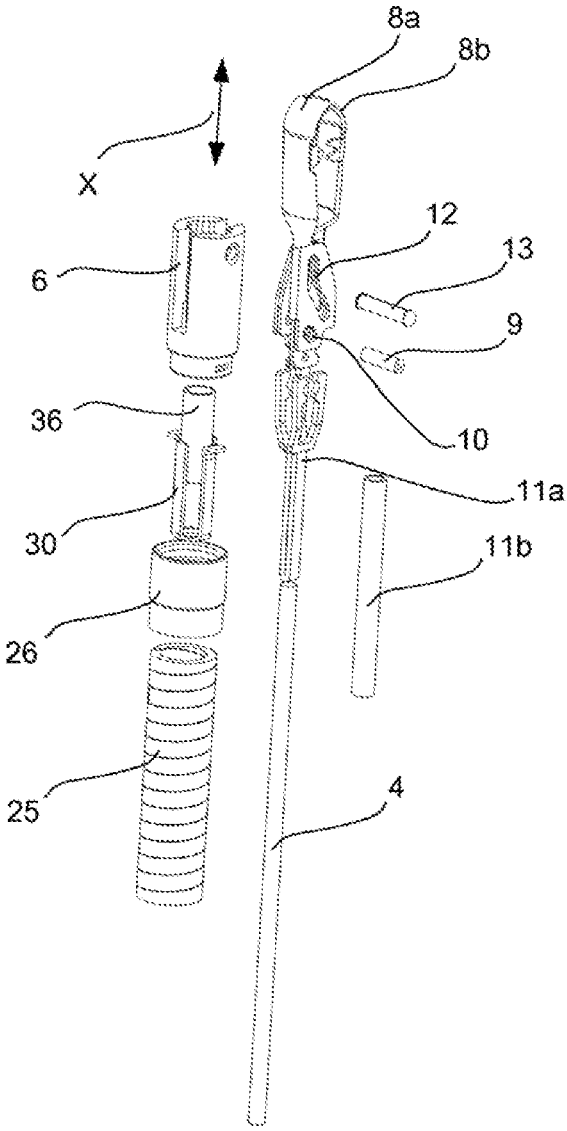
FIG. 3 a perspective exploded view of the distal end of the medical device of FIG. 1.
Figure 4:
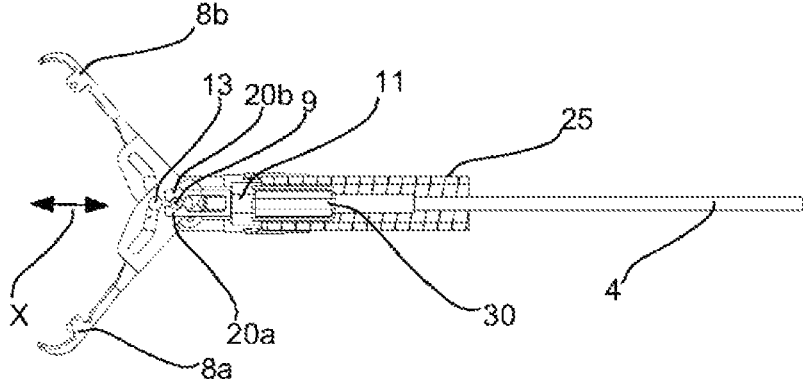
FIG. 4 a cross-sectional view of the distal end of the medical device of FIG. 1 with open clamp arms.
Figure 5:
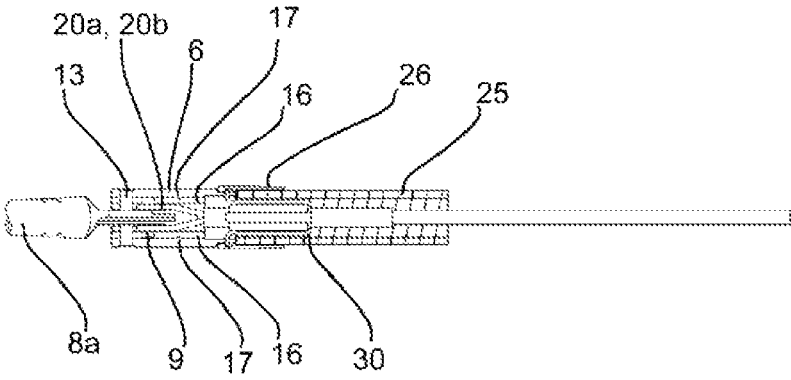
FIG. 5 a cross-sectional view of the distal end of the medical device of FIG. 1 with open clamp arms in another sectional plane.
Figure 6:
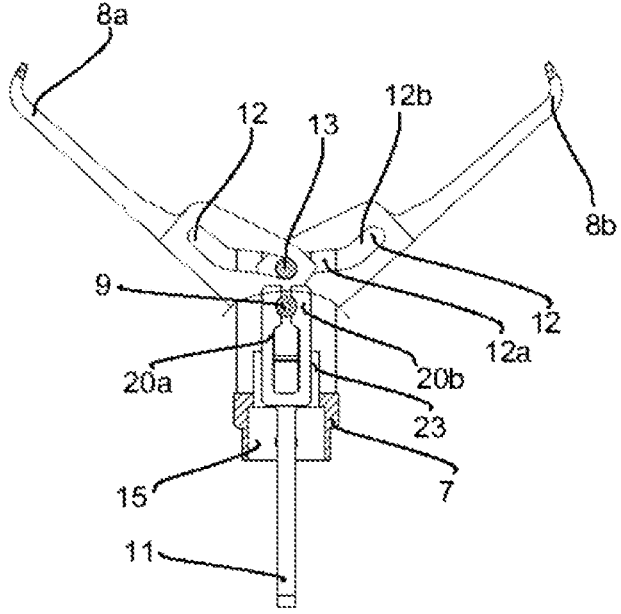
FIG. 6 another cross-sectional view of the distal end of the medical device of FIG. 1 with open clamp arms.
Figure 7:
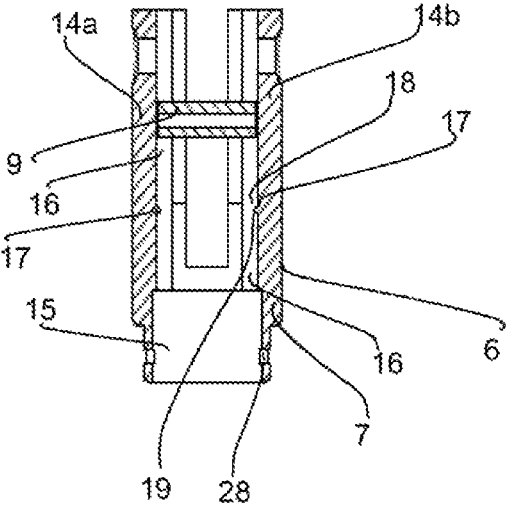
FIG. 7 the clamp base and the pivot pin of the medical device of FIG. 1 in a cross-sectional view with open clamp arms.
Figure 8:
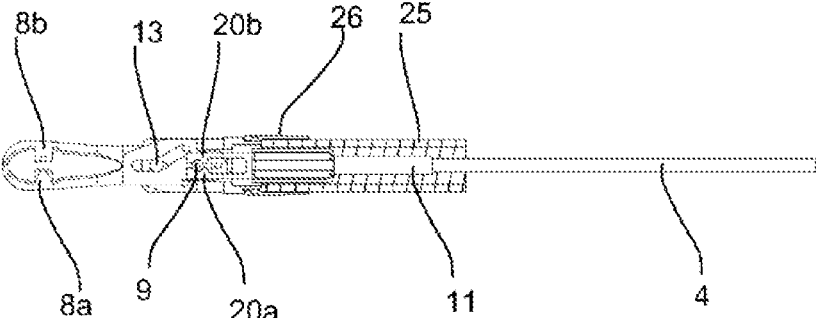
FIG. 8 a cross-sectional view of the medical device of FIG. 1 with closed clamp arms.
Figure 9:
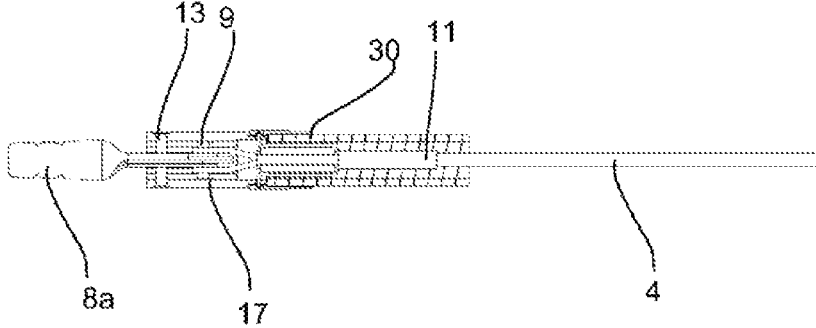
FIG. 9 a cross-sectional view of the distal end of the medical device of FIG. 1 with closed clamp arms in another sectional plane.
Figure 10:
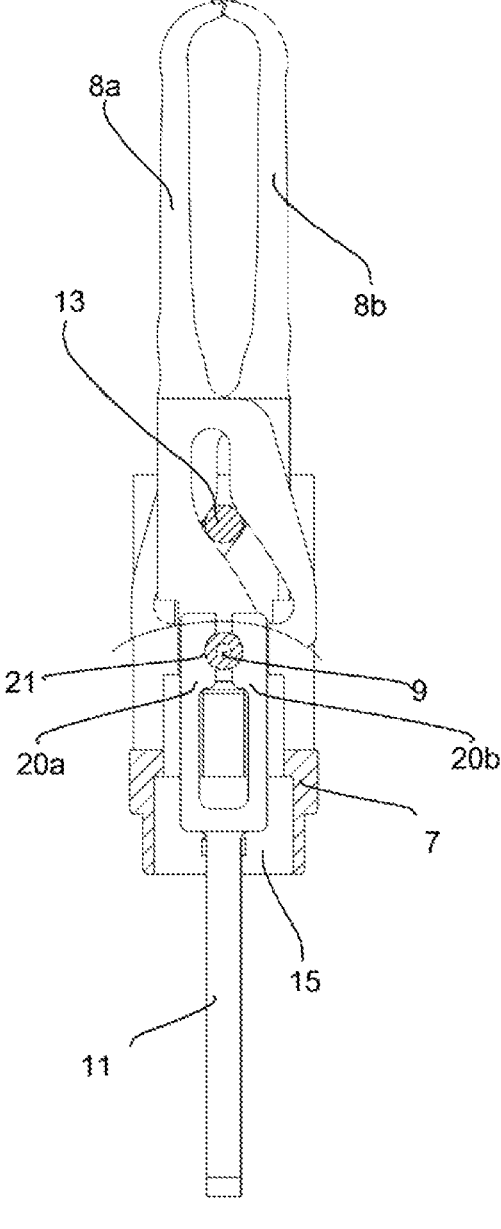
FIG. 10 a cross-sectional view of the distal end of the medical device of claim 1 with closed clamp arms.
Figure 11:
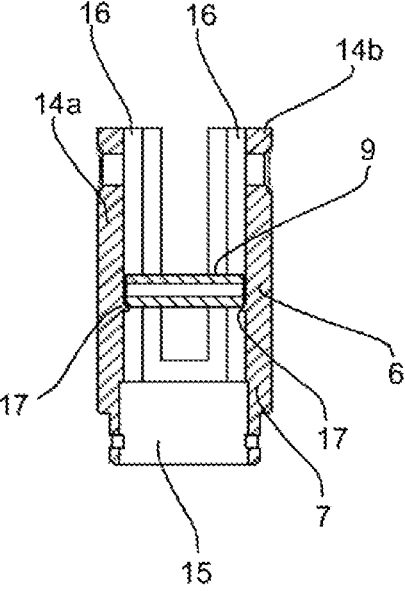
Figure 12:
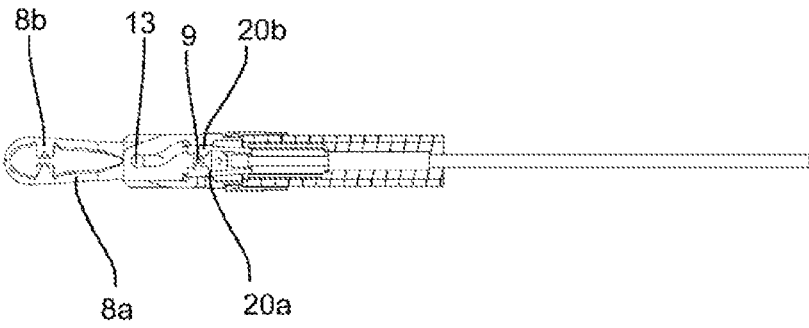
Figure 13:
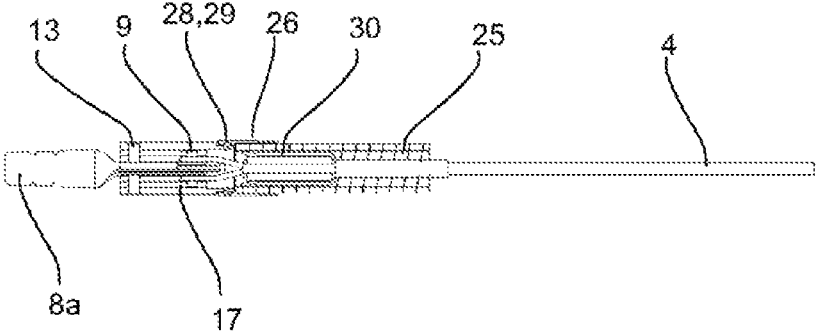
Figure 14:
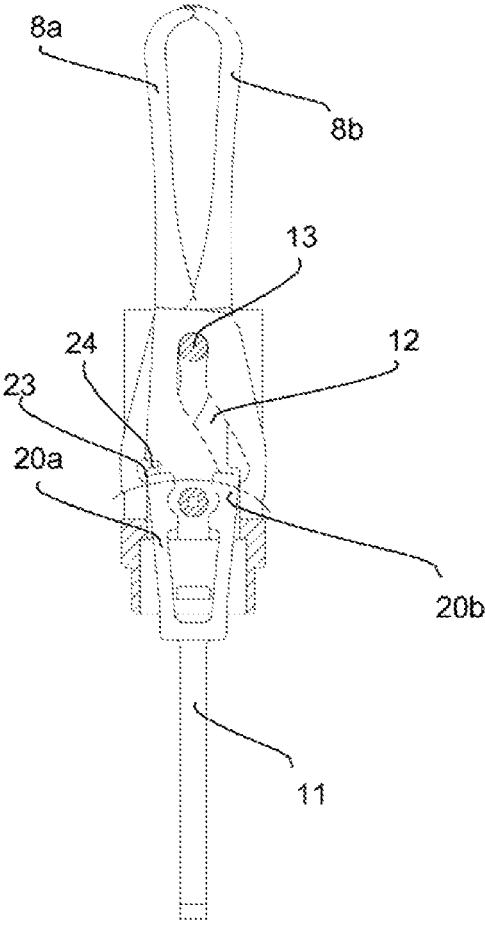
Figure 15:
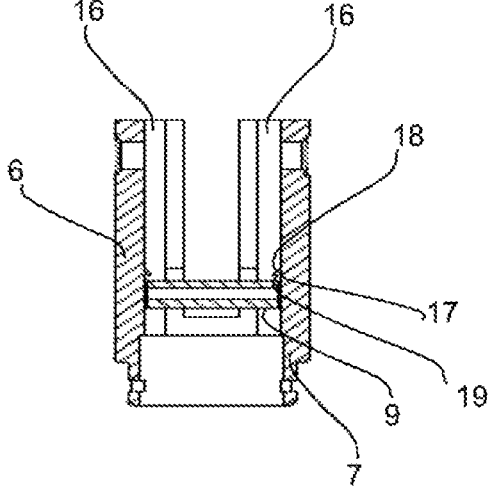
Figure 16:
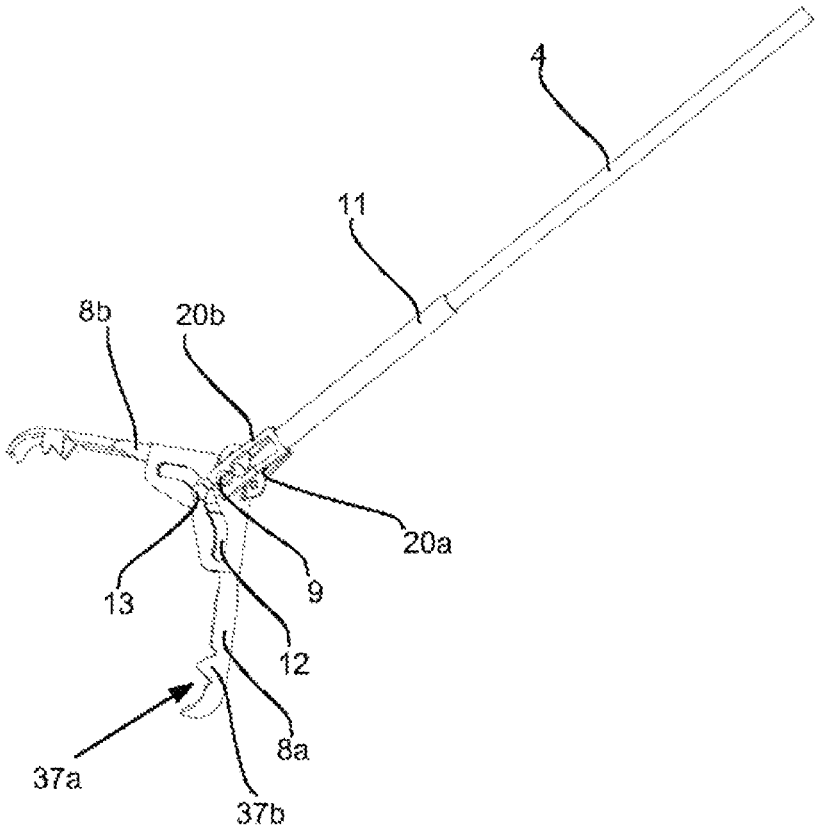
Figure 17:
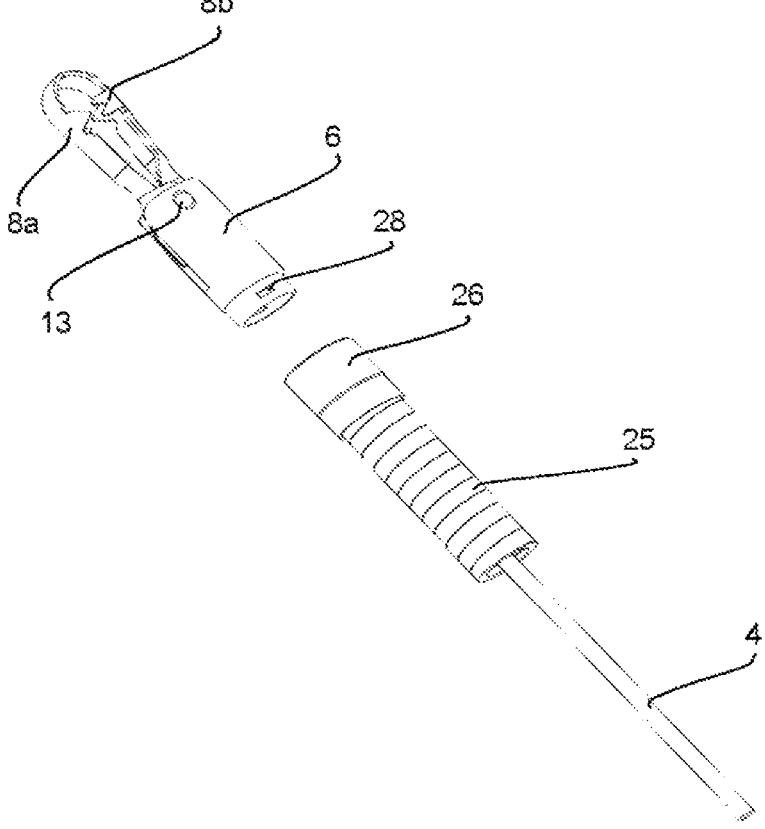
Figure 18:
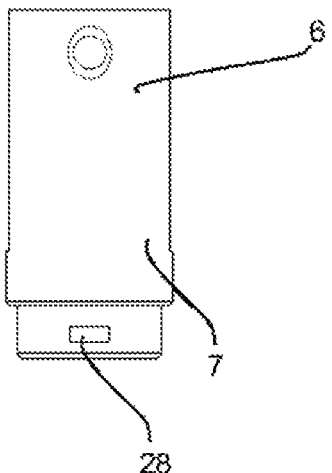
Figure 19:
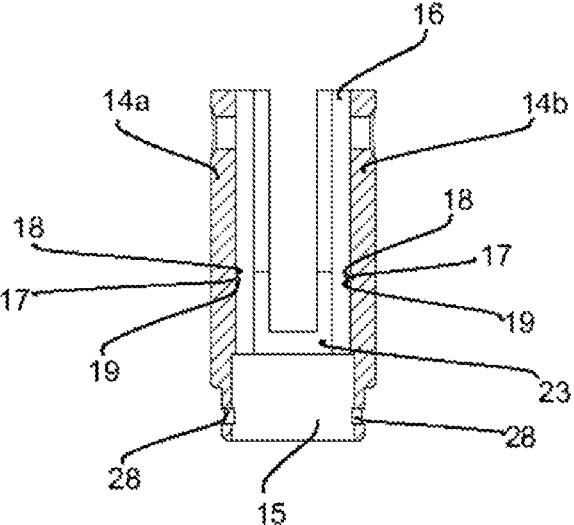
Figure 20:
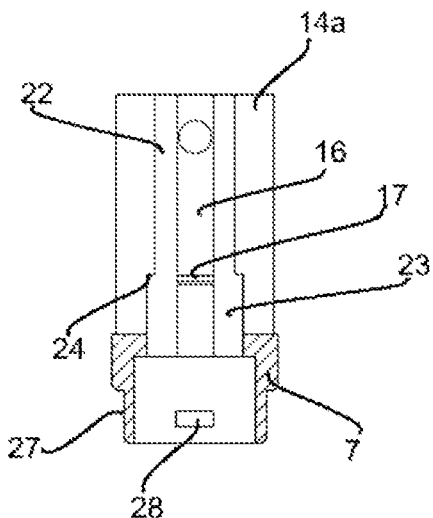
Figure 21:
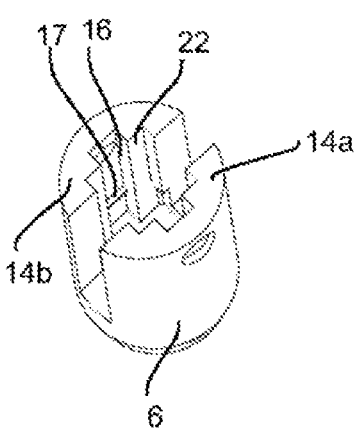
Figure 22:
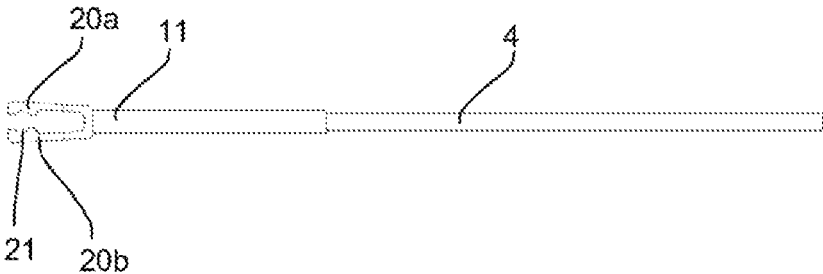
Figure 23:
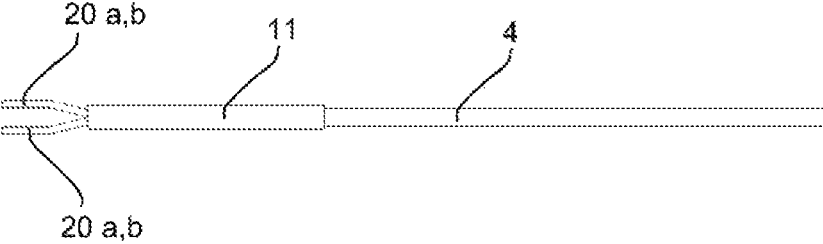
Figure 24:
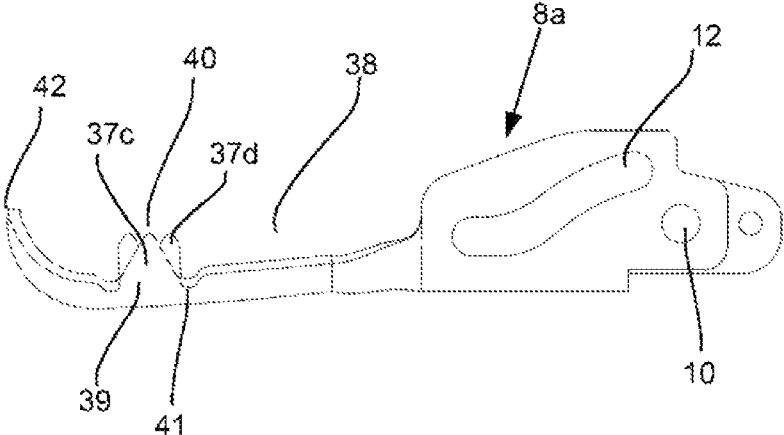
Figure 25:
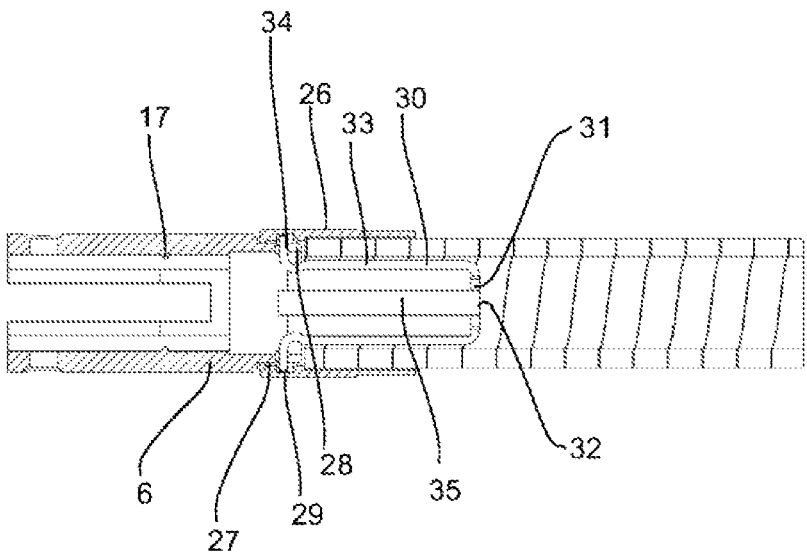
Figure 26:
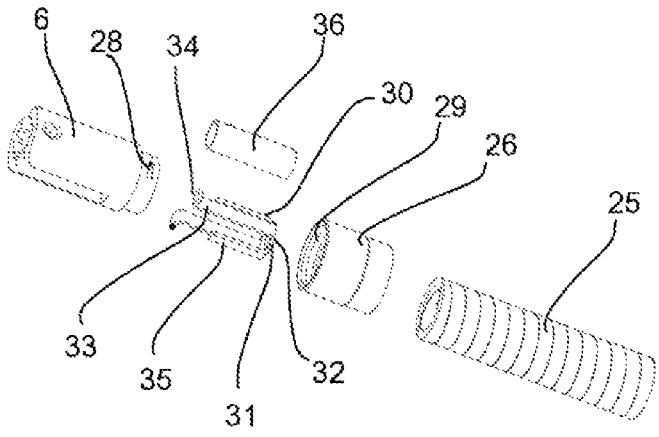
Figure 27:
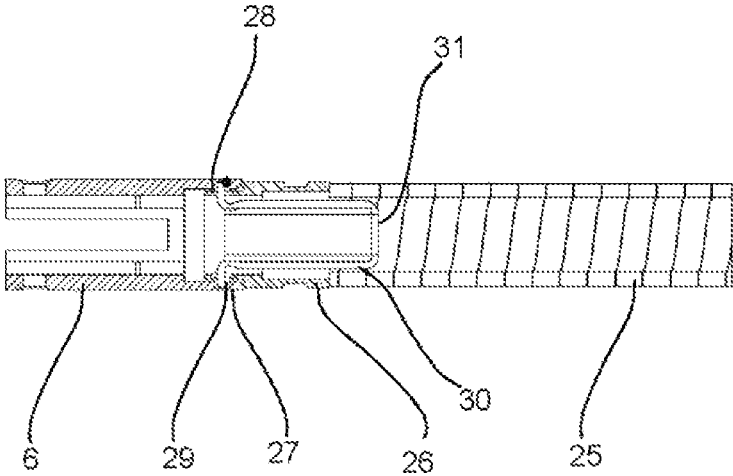
Figure 28:
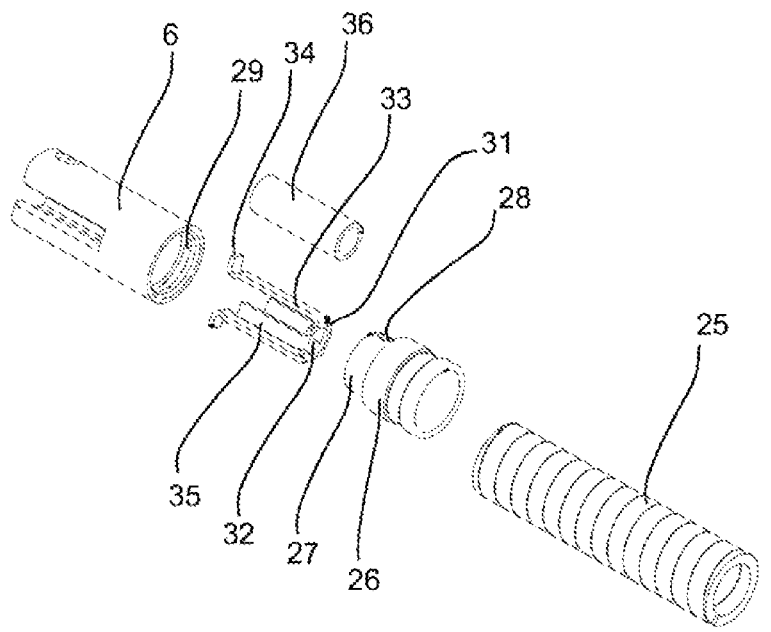
Figure 29:
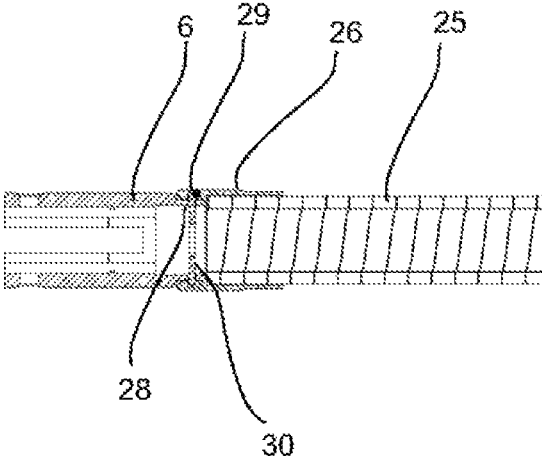
Figure 30:
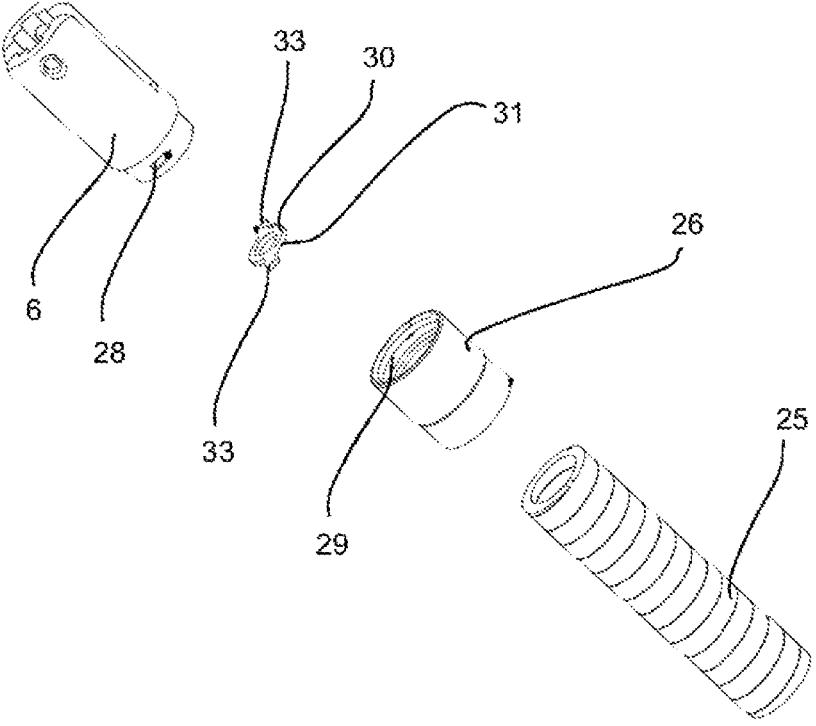
Figure 31:
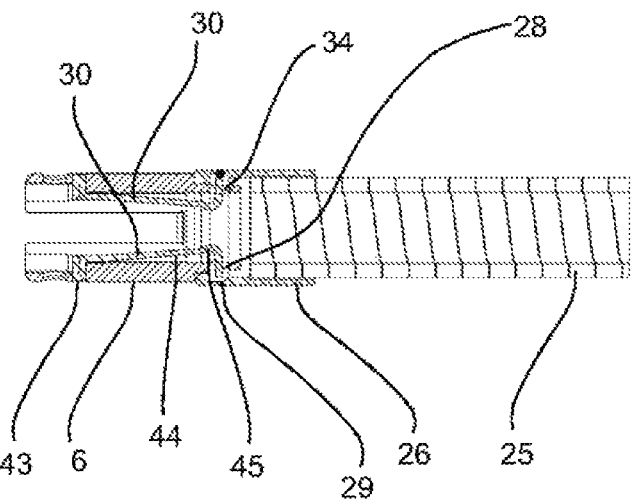
Figure 32:
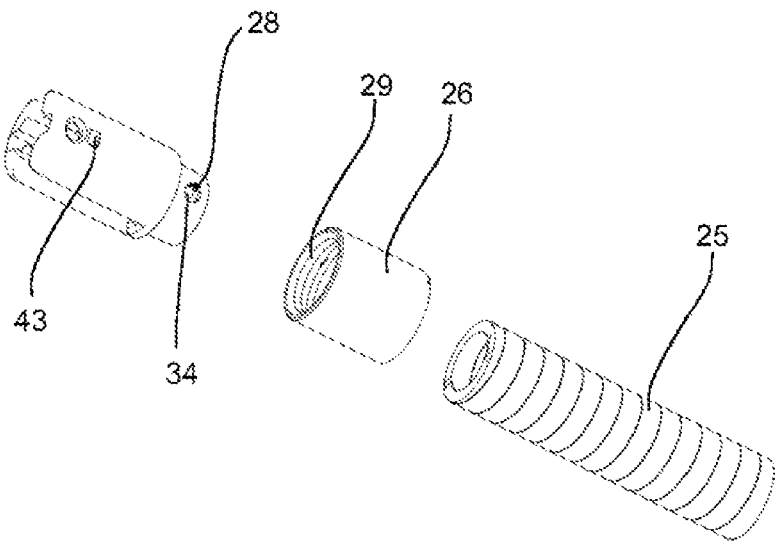

FIG. 11 a cross-sectional view of the clamp base and the pivot pin of the medical device of FIG. 1 with closed clamp arms;

FIG. 12 a cross-sectional view of the distal end of the medical device of FIG. 1 with clamp arms locked in their closed state;

FIG. 13 a cross-sectional view of the distal end of the medical device with clamp arms locked in their closed state in another sectional plane;

FIG. 14 a cross-sectional view of the distal end of the medical device of claim 1 with clamp arms locked in their closed state;

FIG. 15 a cross-sectional view of the clamp base and the pivot pin of the medical device of FIG. 1 with clamp arms locked in their closed state;

FIG. 16 a partial perspective view of the distal end of the control wire and the clamp arms;

FIG. 17 a partial perspective view of the distal end of the medical device with the clamp device released from the sheath device;

FIG. 18 a front view of the clamp base;

FIG. 19 a longitudinal sectional view of the clamp base;

FIG. 20 another longitudinal sectional view of the clamp base;

FIG. 21 a perspective view of the clamp base;

FIG. 22 a side view of the distal end of the control wire with the coupling head;

FIG. 23 a top view of the distal end of the control wire;

FIG. 24 a side view of a clamp arm of the device of FIG. 1;

FIG. 25 a partial cross-sectional view of the distal end of the medical device of FIG. 1;

FIG. 26 a partial exploded view of the distal end of the medical device of FIG. 1 showing the release mechanism of the clamp base and the sheath device;

FIG. 27 a partial cross-sectional view of the distal end of a medical device according to a second embodiment of the present disclosure showing the sheath device, the connecting element and the clamp base;

FIG. 28 a partial exploded view of the distal end of the medical device of FIG. 27;

FIG. 29 a partial cross-sectional view of the distal end of a medical device according to a third embodiment of the present disclosure showing the sheath device, the connecting element and the clamp base;

FIG. 30 a partial exploded view of the distal end of the medical device of FIG. 29;

FIG. 31 a partial cross-sectional view of the distal end of a medical device according to a fourth embodiment of the present disclosure showing the sheath device, the connecting element and the clamp base; and FIG. 32 a partial exploded view of the distal end of the medical device of FIG. 31.

LIST OF REFERENCE NUMERALS IN THE DRAWINGS

1 handle
2 sheath device
3 clamp device
4 control wire
5 actuator
6 clamp housing
7 clamp base
8*a*, 8*b* clamp arm
9 pivot pin
10 through-hole

8

11 coupling head
11*a* sheet-like part
11*b* pressing tube
12 guide groove
12*a* curved section
12*b* straight section
13 guide pin
14*a*, 14*b* bearing arm
15 central passage opening
16 sliding groove
17 locking nose
18 inclined surface
19 surface
20*a*, 20*b* holding arm
21 recess
22 retaining groove
23 enlarged proximal section
24 step
25 sheath
26 connect tube
27 overlapping section
28 through-aperture
29 ring groove
30 connecting element
31 main section
32 central opening
33 connecting arm
34 engagement portion
35 guiding arm
36 intermediate tube
37*a-d* barb
38 grasping section
39 V-shaped protrusion
40 V-shaped recess
41 rounded notch
42 engagement contour
43 holding aperture
44 straight section
45 inwardly bulged section
46 protrusion
X longitudinal direction

DESCRIPTION OF EMBODIMENTS

FIGS. 1 to 26 show a first embodiment of a medical device according to the present disclosure. The medical device is used to set clamps for causing hemostasis of blood vessels located along the gastrointestinal tract, wherein the clamps are delivered to a target site through an endoscope.

The medical device comprises a handle 1, a sheath device 2, which is attached to the handle 1, and a clamp device 3, which is provided on the distal end of the sheath device 2. A control wire 4 extends through the sheath device 2 and is at its proximal end connected to an actuator 5, which is slidingly held on the handle 1 and can be actuated to reversibly move the control wire 4 in the distal and proximal directions. The actuator 5 and the handle 1 are designed in such a way that the control wire 4 can be rotated relative to the sheath device 2 about its longitudinal axis.

The clamp device 3 comprises a clamp housing 6 with a clamp base 7 formed as a sleeve and two clamp arms 8*a*, 8*b*, which are each coupled to the distal end of the control wire 4. Specifically, the two clamp arms 8*a*, 8*b* are separate elements/components, that are coupled to the control wire 4 by means of a pivot pin 9, which is of tubular shape. For this purpose, the pivot pin 9 extends through corresponding through-holes 10 provided in the proximal end sections of the clamp arms 8a, 8b and is releasably held by a coupling head 11 formed at the distal end of the control wire 4.

The two clamp arms 8a, 8b are coupled to the distal end of the control wire 4 so that they can be rotated around a common pivot axis formed by the pivot pin 9 in order to open and close them. Each clamp arm 8a, 8b is provided with a guide groove 12, and the guide grooves 12 of the clamp arms 8a, 8b partially overlap each other. Each guide groove 12 comprises a proximal curved section 12a and a distal straight section 12b. The clamp device 3 further comprises a guide pin 13, which is attached to the clamp housing 6 and extends through the guide grooves 12 in the overlapping parts thereof, so that by the engagement of the guide pin 13 and the guide grooves 12 a movement of the control wire 4 in the proximal direction is translated into a closing movement of the clamp arms 8a, 8b. A movement of the control wire 4 in the distal direction is translated into an opening movement of the clamp arms 8a, 8b around the pivot axis. In the present embodiment, the guide pin 13 is held between two bearing arms 14a, 14b of the clamp housing 6 extending in the distal direction from the clamp base 7 forming a bifurcated structure, the clamp arms 8a, 8b being arranged between those bearing arms 14a, 14b. The clamp housing 6 has an interior space presently defined by a central passage opening 15 formed in the clamp base 7 and the space between the bearing arms 14a, 14b.

The clamp housing 6 has on its inner surface two sliding grooves 16 extending in the longitudinal direction of the clamp housing 6 and arranged opposite each other in such a way that the end sections of the pivot pin 9 engage into the sliding groves 16. The sliding grooves 16 have a rectangular cross-section.

In order to lock the clamp arms 8a, 8b in a closed state, as it is shown in FIGS. 12 to 15, two locking noses 17 are provided on the clamp housing 6. Presently, the locking noses 17 project from the ground of the respective sliding groove 16 into the sliding groove 16 and extend over the entire width of the respective sliding groove 16. The locking noses 17 are designed in such a way that they allow the pivot pin 9 to pass them in the proximal direction but prevent passing of the pivot pin in the distal direction in order to lock the clamp arms 8a, 8b in a closed state. For this purpose, each locking nose 17 has on its distal side an inclined surface 18 having an inclination angle of 45° with respect to the longitudinal direction X of the clamp base 7 and on its proximal side a surface 19 extending perpendicular to the longitudinal direction X.

The medical device further comprises a disengaging arrangement, which allows disconnecting the clamp arms 8a, 8b from the control wire 4, when the clamp arms 8a, 8b are locked in the closed state and the control wire 4 is further pulled in the proximal direction.

For this purpose, the coupling head 11 has a bifurcated holding structure comprising two pairs of holding arms 20a, 20b, which are arranged on laterally opposite sides of the clamp arms 8a, 8b. The holding arms 20a, 20b are movable between a fixing position, which is for example shown in FIGS. 4 to 11, and a disengaging position, which is for example shown in FIGS. 12 to 15. In the fixing position, the holding arms 20a, 20b encompass the pivot pin 9, thus holding the pivot pin 9 in a form-fit manner. In concrete terms, recesses 21 with a semicircular cross-section are formed in the surfaces of the holding arms 20a, 20b facing towards each other. The pivot pin 9 is held in these recesses 21 in the fixing position of the holding arms 20a, 20b. In their disengaging position, the holding arms 20a, 20b are spread apart from each other, thus releasing the pivot pin 9.

The holding arms 20a, 20b are biased towards their disengaging position. As it is visible in particular in FIGS. 2 and 3, the coupling head 11 is formed by a sheet-like part 11a forming the two pairs of holding arms and a pressing tube 11b, by means of which the sheet-like part 11a is connected to the adjacent proximal part of the control wire 4.

The inner contour of the clamp housing 6 cooperates with the holding arms 20a, 20b in such a way that the holding arms 20a, 20b are pressed towards each other into their fixing position as long as the holding arms 20a, 20b extend into a distal section of the clamp housing 6. Presently, the inner contour of the clamp housing 6 comprises one retaining groove 22 assigned to each pair of holding arms 20a, 20b and open towards the distal end of the clamp housing 6. Accordingly, in total two retaining grooves 22 having a rectangular cross-section are located on opposite sides of the interior space of the clamp housing 6. The retaining grooves 22 receive the holding arms 20a, 20b between their side walls such that the holding arms 20a, 20b abut against the side walls and are pressed into their fixing position against their restoring force as long as the holding arms 20a, 20b extend into the retaining groove 22.

The retaining grooves 22 lead proximally into an enlarged proximal section 23 of the clamp housing 6 having an enlarged opening size compared to the retaining groove 22. The transition between the enlarged proximal section 23, which has a substantially rectangular cross-section, and the retaining groove 22 is formed as step 24. Presently, the enlarged proximal section 23 extends over the central passage opening 15 and a proximal part of the bearing arms 14a, 14b. Accordingly, the holding arms 20a, 20b return automatically into their disengaging position due to their restoring force, when the control wire 4 is pulled in the proximal direction such that the holding arms 20a, 20b reach the enlarged proximal section 23.

Presently, the step 24 is arranged with respect to the locking noses 17 in such a way that the pivot pin 9 passes the locking noses 17 before the holding arms 20a, 20b of the coupling head 11 reach the enlarged proximal section 23 and return into their disengaging position. In concrete terms, the step 24 is arranged distally from the locking noses 17. Accordingly, the holding arms 20a, 20b return into their disengaging position before the guide pin 13 reaches the distal end of the straight section 12b of the guide grooves 12.

The sheath device 2 includes a coiled sheath 25, which is connected to the handle 1, and a connect tube 26 fixedly connected, presently welded to the distal end of the sheath 25, so that the sheath 25 and the connect tube 26 form an inseparable unit.

The clamp housing 6 is directly and releasably connected to the connect tube 26 in such a way that the clamp housing 6 can be rotated relative to the connect tube 26 about the longitudinal axis. In concrete terms, this connection is realized by a push-in connection, thus forming an overlapping section 27 of the connect tube 26 and the clamp housing 6. In the embodiment shown in FIGS. 1 to 26, the clamp housing 6 is pushed into the connect tube 26, so that the clamp housing 6 forms an inner element and the connect tube 26 forms an outer element. Two through-apertures 28 are formed in the overlapping section 27 of the clamp housing 6 and a corresponding ring groove 29 facing inwardly is formed in the overlapping section 27 of the connect tube 26.

Presently, one connecting element 30 is provided which engages through the through-apertures 28 into the ring groove 29 in order to connect the clamp housing 6 to the sheath device 2 such that the clamp housing 6 can be rotated relative to the connect tube 26 of the sheath device 2. In concrete terms, the connecting element 30 comprises a proximal main section 31 in the form of a disc having a central opening 32. The control wire 4 passes through this central opening 32. Two connecting arms 33 arranged opposite each other in the circumferential direction extend distally from the main section 31, wherein engagement portions 34 are formed at the distal ends of the connecting arms 33 and extend radially outwardly through the through-apertures 28 into the ring groove 29. Furthermore, the connecting element comprises two guiding arms 35 extending distally from the main section 31. The guiding arms 35 are arranged between the connecting arms 33 in the circumferential direction.

A release arrangement cooperating with the connecting element 30 is provided and can be actuated by moving the control wire 4 in the proximal direction, when the clamp arms 8a, 8b have been closed and the control wire 4 has been uncoupled from the clamp device 3 in order to bring the connecting element 30 out of engagement from the ring groove 29 of the connect tube 26. In concrete terms, the release arrangement comprises an intermediate tube 36 enclosing the control wire 4 and arranged between the connecting element 30 and the coupling head 11 of the control wire 4.

The intermediate tube 36 is designed such that it can push against the main section 31 of the connecting element 30. Accordingly, the intermediate tube 36 can push the connecting element 30 in the proximal direction when the control wire 4 is moved in the proximal direction and the clamp arms 8a, 8b have been closed. In this way, the engagement portions 34 can be brought out of engagement from the ring groove 29 formed in the connect tube 26, thus releasing the clamp housing 6 from the connect tube 26, as it is shown for example in FIG. 13.

In use, the clamp device 3 is delivered to the target site through an endoscope and the clamp device 3 is fixed at a predetermined position on the target site to a blood vessel. For this purpose, the clamp device 3 can be rotated relative to the sheath device 2 by rotating the control wire 4 relative to the sheath device 2. In order to pinch the blood vessel, the clamp arms 8a, 8b can be repeatedly opened and closed by moving the control wire 4 in the distal and proximal direction by means of the actuator 5.

In order to improve the grasping of tissue positioned between the clamp arms 8a, 8b and to minimize the risk of loosening the clamp device 3 when fixed to tissue inside the body of a patient, each clamp arm 8a, 8b comprises two barbs 37a, 37b, 37c, 37d arranged on laterally opposite sides of the clamp arm 8a, 8b in a grasping section 38. The barbs 37a, 37b, 37c, 37d are formed such that each barb points in the direction of a corresponding, opposite barb of the other clamp arm 8a, 8b. For example, on FIG. 24 it is visible that the clamp arm 8b comprises two barbs 37c, 37d pointing towards the other clamp arm 8a. The barb 37c comprises a clamping contour in the form of a V-shaped protrusion 39, wherein the barb 37d comprises a clamping contour in the form of a V-shaped recess 40 which is complementary to the V-shaped protrusion 39. The barb 37a of the clamp arm 8a has a V-shaped recess 40 and the barb 37b has a V-shaped protrusion 39, each complementary to the corresponding barbs 37c, 37d of the other clamp arm 8b. To avoid unintended damages of blood vessels clamped between the clamp arms 8a, 8b, the corners of the V-shaped protrusions 39 and the corners of the V-shaped recesses 40 are rounded. Furthermore, rounded notches 41 are provided adjacent to the barbs 37a, 37b, 37c, 37d.

The distal end of the grasping section 38 of each clamp arm 8a, 8b is bent inwards towards the other clamp arms 8a, 8b. An engagement contour 42, in the present case a zigzag profile, is formed at the distal end of each clamp arm 8a, 8b. The engagement contours 42 of the clamp arms 8a, 8b are complementary to each other so that they engage with each other when the clamp arms 8a, 8b are closed.

Once the clamp device 3 has been set, the clamp arms 8a, 8b are to be locked in their closed state. For this purpose, the control wire 4 is pulled in the proximal direction, so that the pivot pin 9 engaging into the sliding grooves 16 passes the locking noses 17, thereby deforming elastically. When the pivot pin 9 has passed the locking noses 17, it cannot pass again in the distal direction due to the surface 19 extending perpendicular to the longitudinal direction X. In this way, it is prevented, that the clamp arms 8a, 8b can be opened unintentionally again.

As the next step, the clamp arms 8a, 8b are to be disconnected from the control wire 4. For this purpose, the control wire 4 is pulled further in proximal direction so that the holding arms 20a, 20b reach the enlarged proximal section 23 of the clamp housing 6. Due to their elastic restoring force, they spread apart, thus releasing the pivot pin 9 out of the recesses 21 formed in the holding arms 20a, 20b.

In order to uncouple/release the clamp housing 6 from the sheath device 2, the control wire 4 is further pulled back in proximal direction. Accordingly, the intermediate tube 36 is pressed between the coupling head 11 of the control wire 4 and the connecting element 30, thus pushing the connecting element 30 in the proximal direction. In this way, the engagement portions 34 formed at the connecting arms 33 come out of engagement from the ring groove 29 of the connect tube 26 and the through-apertures 28 of the clamp housing 6, so that the clamp housing 6 is released from the connect tube 26 of the sheath device 2.

FIGS. 27 and 28 show a second embodiment of a medical device according to the present disclosure.

This medical device is very similar to the one disclosed in FIGS. 1 to 26 and differs from this embodiment only in that the clamp housing 6 is not pushed into the connect tube 26 fixedly connected to the distal end of the sheath 25, but the clamp housing 6 forming an outer element is pushed onto the connect tube 26, thus forming an inner element. Accordingly, two through-apertures 28 arranged opposite each other are formed in the connect tube 26 and a ring groove 29 facing inwardly is formed in the clamp housing 6.

Consequently, the connecting element 30 formed practically identically to the one in the embodiment shown in FIGS. 1 to 26 engages with its engagement portions 34 of the connecting arms 33 through the through-apertures 28 of the connect tube 26 into the ring groove 29 of the clamp housing 6. In this way, the clamp housing 6 can be rotated relative to the sheath device by rotating the control wire 4.

FIGS. 29 and 30 show a third embodiment of the medical device according to the present disclosure. This medical device is very similar to the one disclosed in FIGS. 1 to 26, but the connecting element 30 differs from the one of the medical device of FIGS. 1 to 26. Presently, the connecting element 30 is formed as a planar disc having a central opening 32 and exactly two connecting arms 33 protruding radially outwardly. As it can be seen in FIG. 29, the connecting arms 33 are arranged in one plane with the disc and engage through the through-apertures 29 formed in the clamp housing 6 into the ring groove 29 formed in the connect tube 26.

In order to release the clamp housing 6 from the connect tube 26, the connecting element 30 is pushed by the coupling head 11 of the control wire 4 in the proximal direction, thus deforming the connecting element 30 and bringing the connecting arms 33 out of engagement from the ring groove 29.

FIGS. 31 and 32 show a further embodiment of the medical device according to the present disclosure.

This medical device is nearly identical to the one previously discussed. However, the sheath device 2 is connected to the clamp housing 6 by means of two connecting elements 30 in the form of elastic connecting arms that are positioned on opposite sides of the clamp housing 6. Specifically, the distal ends of the connecting elements 30 are fixedly attached to the clamp housing 6, whereas the free proximal ends of the connecting elements 30 form engagement portions 34 that engage corresponding engagement means provided in the inner circumferential surface of the connect tube 26 in order to couple the clamp housing 6 to the sheath device 2. Here, the clamp housing 6 is connected to the sheath device 2 by a push-in connection, wherein the proximal end of the clamp housing 6 is inserted/extends into the distal end of the connect tube 26. In the overlapping sections of the connect tube 26, through apertures 28 arranged opposite each other are formed in the clamp housing and a corresponding ring groove 29 is formed in the connect tube 26. The engagement portions 34 of the connecting elements 30 are pressed outwardly through the through-apertures 28 of the clamp housing 6 into the ring groove 29 of connect tube 26 in order to connect the clamp housing 6 to the sheath device 2.

The connecting elements 30 have inwardly bulged sections. Further, the distal ends of the connecting elements 30 are directed radially outwardly and extend into corresponding holding apertures 43 provided in the clamp housing 6 and are preferably fixed therein by welding, presently by a spot welding. The connecting elements 30 further have a straight section 44 following the distal end of the connecting elements 30, which is slanted inwardly with regard to the central longitudinal axis of the clamp housing, wherein the slanting angle is 5°. Between the straight section 44 and the engagement portions 34 of the connecting elements 30 an inwardly bulged section 45 is provided at the proximal end of the connecting elements 30.

A release arrangement for disconnecting the clamp housing 6 from the connect tube 26 is provided. This release arrangement comprises a protrusion 46 formed by the coupling head 11 provided at the distal end of the control wire 4. The protrusion 46 cooperates with and is located between the inwardly bulged sections 45 of the connecting elements 30 to press the inwardly bulged sections 45 outwardly elastically deforming the connecting elements 30 in such a way that their free ends are pressed. When the control wire 4 is pulled proximally and the protrusion 46 comes out of engagement of the connecting elements 30, the bulged sections 45 are redeformed inwardly by their elastic restoring force to obtain their original shape and the engagement portions 34 come out of engagement from the ring groove 29 formed in the connect tube 26.

The invention claimed is:

1. A medical device for causing hemostasis of blood vessel comprising:
a handle;
a sheath device, which is attached to the handle;
a clamp device comprising a clamp housing provided on the distal end of the sheath device and at least two clamp arms;

a control wire extending through the sheath device and reversibly moveable in the distal and proximal direction;
an actuator coupled to the proximal end of the control wire and actuable to reversibly move the control wire in the distal and proximal direction;
wherein the clamp arms are each coupled to the distal end of the control wire and wherein the clamp device is actuable to open and close the clamp arms by a movement of the control wire such that a movement of the control wire in a proximal direction is translated into a closing movement of the clamp arms and a movement of the control wire in the distal direction is translated into an opening movement of the clamp arms;
wherein the sheath device comprises a sheath and a connect tube, which defines a longitudinal axis and is fixedly connected to the distal end of the sheath;
where the clamp housing is directly and releasably connected to the connect tube in such a way that the clamp housing can be rotated relative to the connect tube about the longitudinal axis,
wherein the clamp housing and the connect tube are connected to each other by a push-in connection that forms an overlapping section of the connect tube and the clamp housing,
wherein:
either the clamp housing as an inner element is pushed into the connect tube as an outer element,
or the connect tube as an inner element is pushed into the clamp housing as an outer element,
wherein at least two through-apertures are formed in the overlapping section of the inner element located with an angular offset in the circumferential direction and an inwardly facing ring groove is formed in the overlapping section of the outer element, and
at least one connecting element engages through the at least two through-apertures of the inner element into the ring groove of the outer element to connect the clamp housing to the sheath device such that the clamp housing can be rotated relative to the connect tube of the sheath device.

2. The medical device according to claim 1, further comprising a release arrangement cooperating with each connecting element, wherein the release arrangement is actuated by moving the control wire in the proximal direction when the clamp arms have been closed to bring the connecting element(s) out of engagement from the ring groove of the outer element to release the clamp housing from the sheath device.

3. The medical device according to claim 2, wherein the medical device comprises exactly one connecting element, which has at least two connecting arms located with a regular angular offset in the circumferential direction, each of the connecting arms engaging through one corresponding through-aperture formed in the inner element into the ring groove formed in the outer element.

4. The medical device according to claim 3, wherein the connecting element is formed as a disc having a central opening and at least two connecting arms protruding radially outwardly.

5. The medical device according to claim 4 wherein the release arrangement comprises an intermediate tube enclosing the control wire and arranged between the connecting element and a coupling head formed at the distal end of the control wire so that the intermediate tube pushes the connecting element in the proximal direction when the control wire is moved in the proximal direction and the clamp arms have been closed in order to bring the connecting element out of engagement from the ring groove formed in the outer element, thus releasing the clamp housing from the connect tube.

6. The medical device according to claim 3, wherein the connecting element comprises a proximal main section in the form of a disc having a central opening and at least two connecting arms extending distally therefrom, wherein engagement portions are formed at the distal ends of the connecting arms and extend radially outwardly through the through-apertures of the inner element and into the ring groove formed in the outer element.

7. The medical device according to claim 6, wherein the release arrangement comprises an intermediate tube enclosing the control wire and arranged between the connecting element and a coupling head formed at the distal end of the control wire so that the intermediate tube pushes the connecting element in the proximal direction when the control wire is moved in the proximal direction and the clamp arms have been closed in order to bring the connecting element out of engagement from the ring groove formed in the outer element, thus releasing the clamp housing from the connect tube.

8. The medical device according to claim 2, wherein at least two connecting elements are provided in the form of resilient, elastically deformable connecting arms, wherein the distal ends of the connecting elements are fixedly attached to the clamp housing and the free proximal ends of the connecting elements form engagement portions, each of which engages through a corresponding through-aperture formed in the inner element and into the ring groove formed in the outer element.

9. The medical device according to claim 8, wherein the release arrangement comprises a protrusion, that is arranged between and cooperates with the connecting elements in such a way, that the protrusion presses against the connecting elements elastically deforming them outwardly, so that the engagement portions of the connecting elements are urged outwardly into engagement with a corresponding through-aperture and the ring groove, in order to connect the clamp housing to the sheath device, wherein the protrusion is coupled with the control wire in such a way that, if after closing the clamp arms the control wire is moved further in the proximal direction, the protrusion is moved together with the control wire out of engagement from the connecting elements with the result that the latter are deformed inwardly by their elastic restoring force and the engagement portions of the connecting elements come out of engagement of the corresponding ring groove of the outer element to release the clamp housing from the sheath device.

10. The medical device according to claim 9, wherein the protrusion is formed by a coupling head formed at the distal end of the control wire.

11. The medical device according to claim 1, wherein the connect tube and the sheath are welded or brazed or pressed together.

12. The medical device according to claim 1, wherein the sheath is an extendable coiled sheath.

* * * * *